United States Patent
Takai et al.

(10) Patent No.: US 7,301,068 B2
(45) Date of Patent: Nov. 27, 2007

(54) NONHUMAN MODEL ANIMAL OF TH2-MEDIATED HYPERIMMUNE RESPONSE

(75) Inventors: Toshiyuki Takai, Sendai (JP); Azusa Ujike-Asai, Obu (JP)

(73) Assignee: Japan Science and Technology Corporation, Kawaguchi-shi, Saitana (JP)

( * ) Notice: Subject to any disclaimer, the term of this patent is extended or adjusted under 35 U.S.C. 154(b) by 0 days.

(21) Appl. No.: 10/493,835

(22) PCT Filed: Oct. 25, 2002

(86) PCT No.: PCT/JP02/11105

§ 371 (c)(1),
(2), (4) Date: Nov. 30, 2004

(87) PCT Pub. No.: WO03/037079

PCT Pub. Date: May 8, 2003

(65) Prior Publication Data

US 2005/0091703 A1 Apr. 28, 2005

(30) Foreign Application Priority Data

Oct. 29, 2001 (JP) .............................. 2001-331622

(51) Int. Cl.
*A01K 67/027* (2006.01)
*A01K 67/033* (2006.01)
*G01N 33/00* (2006.01)

(52) U.S. Cl. .............................. 800/18; 800/13; 800/3; 800/21

(58) Field of Classification Search .................... 800/3, 800/8, 21, 18, 13
See application file for complete search history.

(56) References Cited

FOREIGN PATENT DOCUMENTS

JP 2001-161369 6/2001

OTHER PUBLICATIONS

Murrray et al. (1999) Genetic modification of animals in the next century. Theriogenology 51:149-159.*
Kolb et al. (1999) Insertion of a foriegn gene into the beta-casein locus by Cre-mediated site-specific recombination. Gene 227:21-31.*
Houdebine. (2000) Transgenic animal bioreactors. Transgenic Research. 9:305-320.*
Ujike et al. (2002) Impaired dendritic cell maturation and increased Th2 responses in PIR-B-/- mice. Nature Immun. 3:542-548.*
Takai et al. (2000) Cell activation adjusting action of paired immunoglobulin-like receptor (PIR) Ann. Rev. Immunity. pp. 320-327. (English Translation).*
Majzoub et al. (1996) N. Eng. J. Med. 334:904-7.*
Maeda et al. (1998) J. Exp. Med. 188:991-995.*
Uehara et al. (20001) J. Clin. Invest 108:1041-1050.*
Mansour, S.L. et al. "Disruption of the proto-oncogene int-2 in mouse embryo-derived stem cells: a general strategy for targeting mutations to non-selectable genes," Nature, vol. 336:24, 348-352, Nov. 24, 1998.
Schopf, L.R. et al., "Interleukin-12 Is Capable of Generating an Antigen-Specific Th1-Type Response in the Presence of an Ongoing Infection-Driven Th2-Type Response," Infection and Immunity, vol. 67, No. 5, 2166-2171, 1999.
Maeda, A. et al., "Requirement of SH2-containing Protein Tyrosine Phosphatases SHP-1 and SHP-2 for Paired Immunoglobulin-like Receptor B (PIR-B)-mediated Inhibitory Signal," J. Exp. Med., vol. 187, No. 8, 1355-1360, Apr. 20, 1998.
Yamashita, Y. et al., "Inhibitory and Stimulatory Functions of Paired Ig-Like Receptor (PIR) Family in RBL-2H3 Cells[1]," J. Immunol, vol. 161, No. 8, 4042-4027, 1998.
Bléry, M. et al., "The paired Ig-like receptor PIR-B is an inhibitory receptor that recruits the protein-tyrosine phosphatase SHP-1," Proc. Natl. Acad. Sci. USA, vol. 95, 2446-2451, Mar. 1998.
Kubagawa, H. et al., " A novel pair of immunoglobulin-like receptors expressed by B cells and myeloid cells," Proc. Natl. Acad. Sci, USA, vol. 94, 5261-5266, May 1997.
Hayami, K. et al., "Molecular Cloning of a Novel Murine Cell-surface Glycoprotein Homologous to Killer Cell Inhibitory Receptors," J. Biol. Chem., vol. 272, No. 11, 7320-7327, Mar. 14, 1997.
PCT/JP2002/011105: Form PCT/IPEA/409, dated Sep. 8, 2003 and Form PCT/IB/338, dated May 27, 2004, WIPO.
Supplementary European Search Report for corresponding Euopean national phase application No. 02777958 of the PCT Application No. PCT/JP02/11105, completion date of the European search of Mar. 23, 2007; date of mailing Apr. 16, 2007.
Takai T, Ujike A, Takeda K, Nakamura A, Ebihara S, Akiyama K, "Hypersensitive B cells and Th2-prone immune responses in paired immunoglobulin-like receptor (PIR)-B-deficient mice" FASEB 2002, vol. 16, No. 4, p. A313 & "ABSTRACT—Hypersensitive B cells and Th2-prone immune responses in paired immunoglobulin-like receptor (PIR)-B-deficient mice", Annual Meeting of the Professional Research Scientists on Experimental Biology, New Orleans, Lousiana, USA, Apr. 20-24, 2002.

(Continued)

*Primary Examiner*—Anne M. Wehbe'
(74) *Attorney, Agent, or Firm*—Morgan & Finnegan, L.L.P.

(57) ABSTRACT

An object of the present invention is to provide a nonhuman model animal of Th2-mediated hyperimmune response lacking PIR-B gene function on its chromosome by which the Th2-mediated immune response mechanism and allergy onset mechanism in vivo can be analyzed and which is liable to suffer from not only hyper-response of B cells but also allergy, and an inducer/promoter or an inhibitor for Th2-mediated immune response, etc. with the use of the nonhuman model animal of Th2-mediated hyperimmune response. The nonhuman model animal of Th2-mediated hyperimmune response is prepared by integrating a fragment comprising exons 1 to 7 and the domain in the 5' side of exon 8 of mouse PIR-B gene and another fragment containing exons 10 to 14 into a vector pMC1-Neo, cleaving it with Xho I-Sal I, integrating it into a vector pIC19R-MC1tk having herpes virus thymidine kinase to thereby construct targeting vector, transferring the targeting vector into ES cells and then injecting the ES cells into blastcyst.

11 Claims, 6 Drawing Sheets

OTHER PUBLICATIONS

Takai T, Ono M., "Activating and inhibitory nature of the murine paired immunoglobulin-like receptor family", *Immunol Rev.* 2001, vol. 181, No. 1, pp. 215-222.

Chen CC, Hurez V, Brockenbrough JS, Kubagawa H, Cooper MD, "Paternal monoallelic expression of the paired immunoglobulin-like receptors PIR-A and PIR-B", *Proc Natl Acad Sci U S A*, Jun. 8, 1999;96(12):6868-72 & "ABSTRACT—Paternal monoallelic expression of the paired immunoglobulin-like receptors PIR-A and PIR-B", *Annual Meeting of the Professional Research Scientists on Experimental Biology*, New Orleans, Lousiana, USA, Apr. 20-24, 2002.

Ono M, Yamashita Y, Ra C, Takai T, "Inhibitory and stimulatory functions of the paired immunoglobulin-like receptor (PIR) family in mast cells" FASEB J. 1999, vol. 13 No. 4, p. A323 & "ABSTRACT—Inhibitory and stimulatory functions of the paired immunoglobulin-like receptor (PIR) family in mast cells", *Annual Meeting of the Professional Research Scientists for Experimental Biology 99*, Washington, DC, Apr. 17-21, 1999.

Kubagawa H, et al., "Biochemical nature and cellular distribution of the paired immunoglobulin-like receptors, PIR-A and PIR-B", *Journal of Experimental Medicine* 1999, vol. 189, No. 2, pp. 309-317.

Ono M, Yuasa T, Ra C, Takai T, "Stimulatory function of paired immunoglobulin-like receptor-A in mast cell line by associating with subunits common of Fc receptors" *J. Biol Chemistry* 1999, vol. 274, No. 42, pp. 30288-30296.

\* cited by examiner

SEQUENCE LISTING

```
<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Primer 1

<400> SEQUENCE: 1
tatcctcgag cttctccgac gaagacatcg                              30

<210> SEQ ID NO 2
<211> LENGTH: 31
<212> TYPE: DNA
<213> ORGANISM: Artificial Sequence
<220> FEATURE:
<223> OTHER INFORMATION: Primer 2

<400> SEQUENCE: 2
agatcgtcga ctgttcagtt gttcccttga c                            31
```

US 7,301,068 B2

NONHUMAN MODEL ANIMAL OF TH2-MEDIATED HYPERIMMUNE RESPONSE

TECHNICAL FIELD

The present invention relates to a nonhuman model animal of Th2-mediated hyperimmune response lacking the function of PIR-B gene on its chromosome, which is an inhibitory receptor gene of paired immunoglobulin (Ig)-like receptor family liable to suffer from not only hyper-response of B cells but also allergy. Further, the present invention relates to a method for screening an inducer/promoter or an inhibitor for Th2-mediated immune response or a promoter or an inhibitor for PIR-A function, and a method for screening a therapeutic agent for allergosis.

BACKGROUND ART

T cells controlling humoral immunity and cellular immunity are mostly $CD4^+T$ cells, which can be classified into Th (helper T cells) 1 or Th2 cells respectively, by patterns for producing cytokine. Th1 cells are known to produce IFN-γ and IL (interleukin) -2 and induce activation of macrophage, while Th2 cells are known to promote activation and antibody generation of B cells by secreting IL-4, IL-5, IL-10, IL-13 and the like. Currently, the studies related to differentiation of Th1 and Th2 has gathered attention, since they are thought to be deeply involved in the cause of immune mediated illness. Th1 has been suggested its relevance to delayed-type allergy and organ-specific autoimmune disease, whereas Th2 has been suggested its relevance to type 1 allergy and systemic autoimmune disease (SLE and others). However, because they are in antagonistic relationship each other, these diseases are expected that they can be prevented or treated by controlling Th1 or Th2. Indeed, it has been reported that administering IL-12 with an antigen for infectious disease such as leishmania induces Th1 preventing development to forfend infection.

On the other hand, PIR of mice whose expression is found in B cells, mast cells, dendritic cells and macrophages are type 1 transmembrane-type glycoprotein, belonging to immunoglobulin (Ig)-like receptor family, have 6 Ig domains extracellularly and they are classified into two subtypes of PIR-A and PIR-B by their differences of intracellular structure. The immunoglobulin (Ig)-like receptors PIR-A and PIR-B (J. Biol. Chem. 272, 7320-7327, 1997; Proc. Natl. Acad. Sci. USA. 94, 5261-5266, 1997) have been known to be the activating-type or inhibitory receptors of Ig-like receptor (IgLR) family expressing in a pair-wise fashion on a wide variety of cells mostly in the immune system (Science 290, 84-89, 2000). It has been reported that aforementioned PIR-A requires Fc receptor γ chain for its expression on cell surface and for delivery of activation signaling (J. Exp. Med. 188, 991-995, 1998; J. Exp. Med. 189, 309-318, 1999; J. Immunol. 161, 4042-4047, 1998; J. Biol. Chem. 274, 30288-30296, 1999). In contrast, PIR-B has been reported that it contains immunoreceptor tyrosine-based inhibitory motifs (ITIMs) in its cytoplasmic portion and inhibits receptor-mediated activation signaling in vitro by engaging antigen receptor (BCR) on B cells and other activating-type receptors (J. Immunol. 161, 4042-4047, 1998; Proc. Natl. Acad. Sci. USA. 95, 2446-2451, 1998; J. Exp. Med. 187, 1355-1360, 1998). However, neither the physiological function nor ligand for PIR has been elucidated yet.

An object of the present invention is to provide a nonhuman model animal of Th2-mediated hyperimmune response lacking PIR-B gene function on its chromosome by which the Th2-mediated immune response mechanism and allergy onset mechanism in vivo can be analyzed and which is liable to suffer from not only hyper-response of B cells but also allergy, and to provide a method for screening an inducer/promoter or an inhibitor for Th2-mediated immune response, or a promoter or an inhibitor for PIR-A function, a method for screening a therapeutic agent for allergosis and a method for diagnosing allergosis with the use of the nonhuman model animal of Th2-medeated hyperimmune response.

The present inventors have made a keen study to elucidate physiological function for PIR-B being an inhibitory receptor pairs in the paired immunoglobulin-like receptor family, and have found that the mice lacking PIR-B gene function on its chromosome show Th2-prone humoral responses which are liable to suffer from not only hyper-response of B cells but also allergy to complete the present invention. That is, the present invention has completed based on the findings as follows. Examining above-mentioned PIR-B-deficient (PIR-B$^{-/-}$) mice revealed that they have increased the number of peritoneal B-1 cells and that the B-1 cells and splenic B-2 cells of the PIR-B-$^{-/-}$ mice showed hypersensitivity to BCR. The nonhuman model animal of Th2-mediated hyperimmune response has been constructed based on this knowledge. In addition, immunizing PIR-B-$^{-/-}$ mice with T-indepenent (TI) antigens showed the enhanced IgM response compared with wild-type mice. It is thus found that PIR-B comprises an inhibitory ability for activation signaling via BCR under physiological conditions and it can down-regulate the size of the B-1 cell population. Moreover, immunizing PIR-B$^{-/-}$ mice with TD antigens (an alum adjuvant mixed with TNP-KLH which initiates Th2-type response and pertussis toxin) allowed the present inventors to find that the antibody titer of IgG1 was especially rose and IL-4 production in PIR-B-deficient mice was dominantly increased compared to wild-type mice. From these points of view, it has been shown that PIR-B-deficient mice exhibit Th-2-type prone humoral response, which might be caused by the impaired maturation of dendritic cells (DCs) in PIR-B$^{-/-}$ mice. Furthermore, in the present invention, based on this knowledge, a method for screening an inducer/promote or an inhibitor for Th2-mediated immune response or a promoter or an inhibitor for PIR-A function, a method for screening a therapeutic agent for allergosis, a method for diagnosis of allergosis and the like have been constructed.

DISCLOSURE OF THE INVENTION

The present invention relates to a nonhuman model animal of Th2-mediated hyperimmune response which induces hyper-response of a B cell and facilitates development of an allergy by lacking PIR-B gene function on its chromosome ("1"); the nonhuman model animal of Th2-mediated hyperimmune response according to "1", wherein it develops the allergy more excessively than a wild-type nonhuman animal by immunizing an adjuvant that initiates Th2-mediated response ("2"); the nonhuman model animal of Th2-mediated hyperimmune response according to "2", wherein the adjuvant that initiates Th2-mediated response is an alum adjuvant comprising a TNP-KLH and a pertussis toxin ("3"); and the nonhuman model animal of Th2-mediated hyperimmune response according to any one of "1" to "3", wherein the nonhuman animal is a mouse ("4").

The present invention also relates to a method for screening an inducer/promoter or an inhibitor for Th2-mediated immune response or a promoter or an inhibitor for PIR-A function, wherein an alteration of Th2-mediated immune response or PIR-A function is determined/evaluated by administering a test substance to the nonhuman model animal of Th2-mediated hyperimmune response according to any one of "1" to "4" or contacting a tissue, an organ or a cell derived from the animal to the test substance ("5"); the method for screening an inducer/promoter or an inhibitor for Th2-mediated immune response or a promoter or an inhibitor for PIR-A function according to "5", wherein the alteration of Th2-mediated immune response is an alteration of activation of the B cell, generation of antibody, production of cytokine and/or antigen presentational ability in an antigen presenting cell ("6"); the method for screening an inducer/promoter or an inhibitor for Th2-mediated immune response or a promoter or an inhibitor for PIR-A function according to "6", wherein the alteration of activation of the B cell is an alteration of development or proliferation of the B cell ("7"); the method for screening an inducer/promoter or an inhibitor for Th2-mediated immune response or a promoter or an inhibitor for PIR-A function according to "6", wherein the alteration of generation of antibody is an alteration of generation of an IgM antibody, an IgG1 antibody, an IgG2b antibody and/or an IgG2a antibody ("8"); the method for screening an inducer/promoter or an inhibitor for Th2-mediated immune response or a promoter or an inhibitor for PIR-A function according to "6", wherein the alteration of production of cytokine is an alteration of production of interleukin-4, IFN-γ and/or interleukin-12 ("9"); the method for screening an inducer/promoter or an inhibitor for Th2-mediated immune response or a promoter or an inhibitor for PIR-A function according to "6", wherein the alteration of antigen presentational ability in the antigen presenting cell is an alteration of expression amount of a major histocompatibility complex class II, CD80 and/or CD 86 in a dendritic cell ("10"); and the method for screening an inducer/promoter or an inhibitor for Th2-mediated immune response or a promoter or an inhibitor for PIR-A function according to any one of "5" to "10", wherein a case with the nonhuman model animal of Th2-mediated hyperimmune response according to any one of "1" to "4" is compared/evaluated with a case with the wild-type nonhuman animal ("11").

The present invention further relates to a method for screening a therapeutic agent for an allergosis, wherein the alteration of Th2-mediated immune response or PIR-A or PIR-B function is determined/evaluated by administering a Th2-mediated immune response initiating adjuvant and the test substance to the nonhuman model animal of Th2-mediated hyperimmune response according to any one of "1" to "4", or contacting the tissue, the organ or the cell derived from the animal to the Th2-mediated immune response initiating alum adjuvant and the test substance ("12"); the method for screening a therapeutic agent for an allergosis wherein the alteration of Th2-mediated immune response is an alteration of activation of the B cell, generation of antibody, production of cytokine and/or antigen presentational ability in the antigen presenting cell ("13"); the method for screening a therapeutic agent for an allergosis according to "13", wherein the alteration of the B cell is an alteration of development or proliferation of the B cell ("14"); the method for screening a therapeutic agent for an allergosis according to "13", wherein the alteration of generation of antibody is an alteration of generation of an IgM antibody, an IgG1 antibody, an IgG2b antibody and/or an IgG2a antibody ("15"); the method for screening a therapeutic agent for an allergosis according to "13", wherein the alteration of production of cytokine is an alteration of production of interleukin-4, IFN-γ and/or interleukin-12 ("16"); and the method for screening a therapeutic agent for an allergosis according to "13", wherein the alteration of antigen presentational ability in the antigen presenting cell is an alteration of expression amount of the major histocompatibility complex class II, CD80 and/or CD 86 in the dendritic cell ("17").

The present invention still further relates to an inducer/promoter or an inhibitor for Th2-mediated immune response or a promoter or an inhibitor for PIR-A function obtained by the method for screening an inducer/promoter or an inhibitor for Th2-mediated immune response or a promoter or an inhibitor for PIR-A or PIR-B function according to any one of "5" to "11" ("18"); the inducer/promoter or the inhibitor for Th2-mediated immune response or the promoter or the inhibitor for PIR-A function according to "18", wherein the inducer/promoter or the inhibitor for Th2-mediated immune response is a therapeutic agent for a disorder attributed to Th2-mediated hyperimmune response ("19"); the inducer/promoter or the inhibitor for Th2-mediated immune response or the promoter or the inhibitor for PIR-A function according to "19", wherein the disorder attributed to Th2-mediated hyperimmune response is an allergosis ("20"); a therapeutic agent for an allergosis obtained by the method for screening a therapeutic agent for an allergosis according to any one of "12" to "17" ("21"); a method for diagnosis of an allergosis wherein a disease symptom of the nonhuman model animal of Th2-mediated hyperimmune response according to any one of "1" to "4" is utilized therefor ("22").

Figure 1:
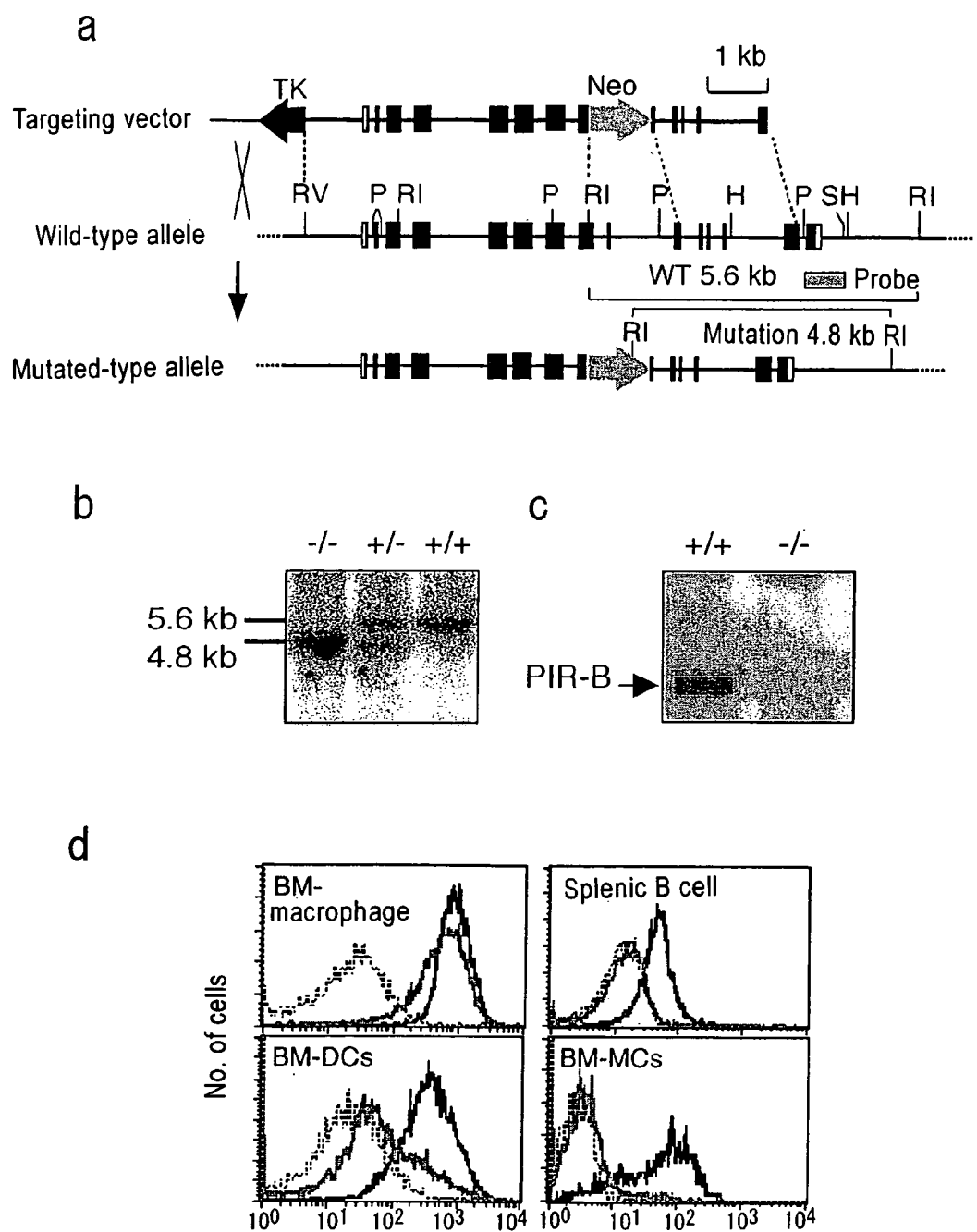
FIG. 1 shows graphs indicating a gene map of PIR-B knockout mice of the present invention and wild-type mice (a), the result of Southern blot analysis in each mouse (b), the result of immunoblot analysis (c) and the result of flow cytometric analysis of expression of PIR on cell surface of BM-macrophages, BM-DCs, splenic B cells, and BM-MCs, respectively.

(a) Organization of PIR-B gene, construction of the targeting vector (TK: thymidine kinase gene, Neo: neomycin resistance gene), and the structure of the targeted genome are shown. In the drawing, H, P, RI, RV and S represent the restriction site of Hin dIII, Pst I, Eco RI, Eco RV and Sph I, respectively.

(b) Genomic DNA from homozygotic mice of littermates obtained from intercrossing heterozygotes was cleaved with Eco RI, and the resulting fragments were subjected to Southern blot analysis with a probe of FIG. 1a (Pst 1-Sph 1 fragment). The positions of 5.6 kb and 4.8 kb represent wild-type allele (+) and mutated form allele (−), respectively.

(c) Splenic B cells ($2 \times 10^6$ cells) from wild-type mice (+/+) or PIR-B$^{-/-}$ mice (−/−) were subjected to immunoblot analysis using goat anti-PIR polyclonal antibodies. Position of PIR-B of approximately 120-kDa is indicated by an arrow.

(d) The cells from wild-type (deep-colored line) or those from PIR-B$^{-/-}$ mice (light-colored line) were reacted with phycoerythrin (PE)-conjugated anti-mouse PIR-A/B antibody (6C1) or PE-conjugated rat IgG1 monoclonal antibody (dotted line; control), stained with FITC-labeled monoclonal antibodies such as anti-CD11b antibody, anti CD11c antibody, anti B220 antibody, or anti-c-kit antibody to separate positive cells.

Figure 2:
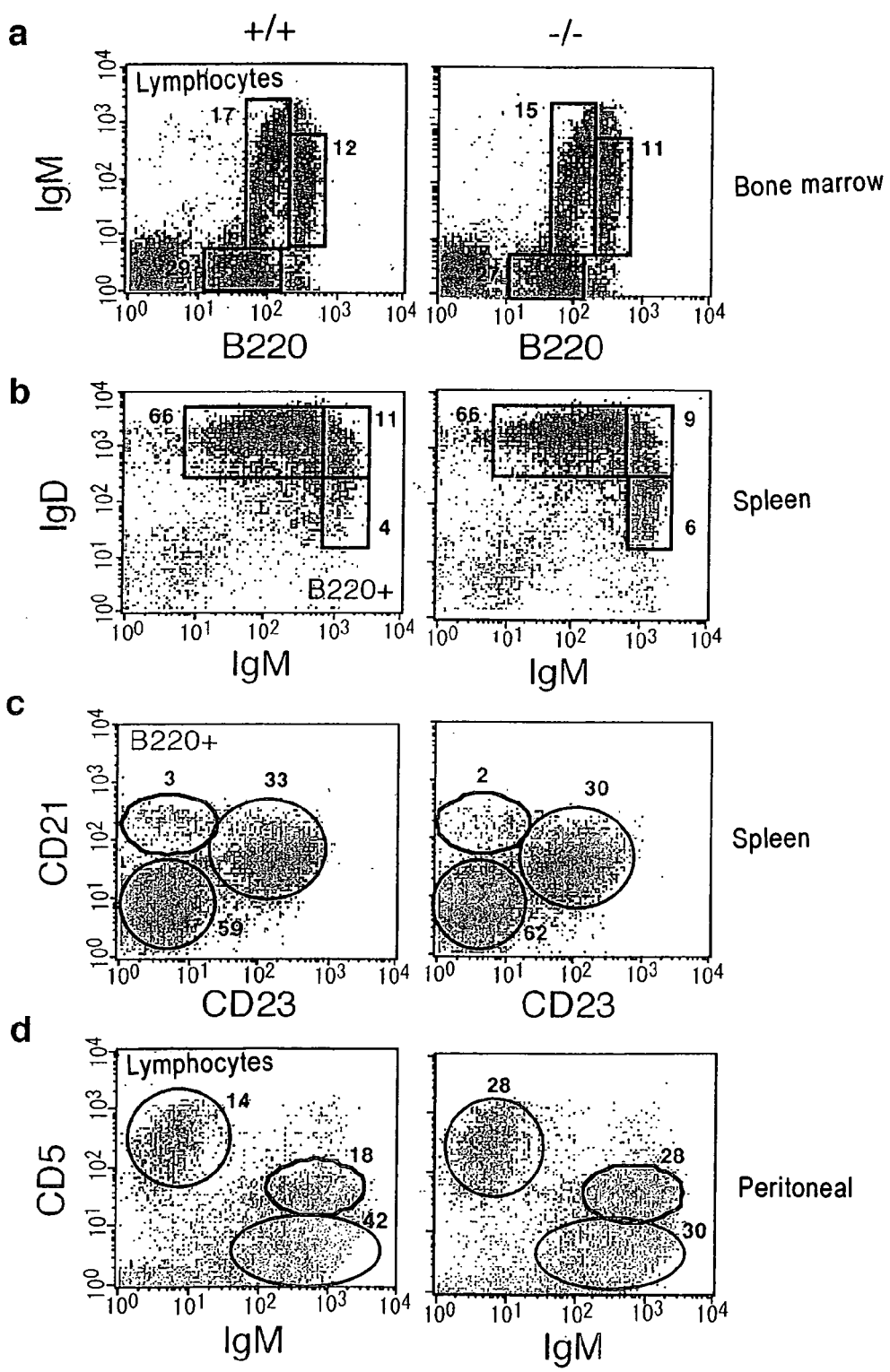

FIG. 2 shows graphs indicating the results of analysis of development of B cells in PIR-B$^{-/-}$ mice of the present invention and wild-type mice by flow cytometry.

(a) Bone-marrow cells were stained with B220 and IgM, and separated pro, pre, immature and mature B cells by flow cytometric analysis.

(b) Splenic B220 positive cells were stained with IgM and IgD and separated to show mature IgM$^{lo}$IgD$^{hi}$ B cells, type 2 transitional B cells (T-2 B cells) of IgM$^{hi}$IgD$^{hi}$, and type 1 transitional B cells (T-1 B cells) of IgM$^{hi}$IgD$^{lo}$.

(c) Splenic B220 positive cells were stained with CD21 and CD23 and separated to show newly formed CD21$^-$CD23$^-$ B cells, CD21$^+$CD23$^+$ B cells and CD21$^+$CD23$^-$ B cells.

(d) Peritoneal cells were stained with CD5 and IgM, and separated leukocytes to show CD5$^+$IgM$^+$B-1 cells.

The numbers near fractions in each of the graphs represent the ratios of cells existing in fractions in all cells. The result of each panel indicates the mean obtained from three independent experiments.

Figure 3:
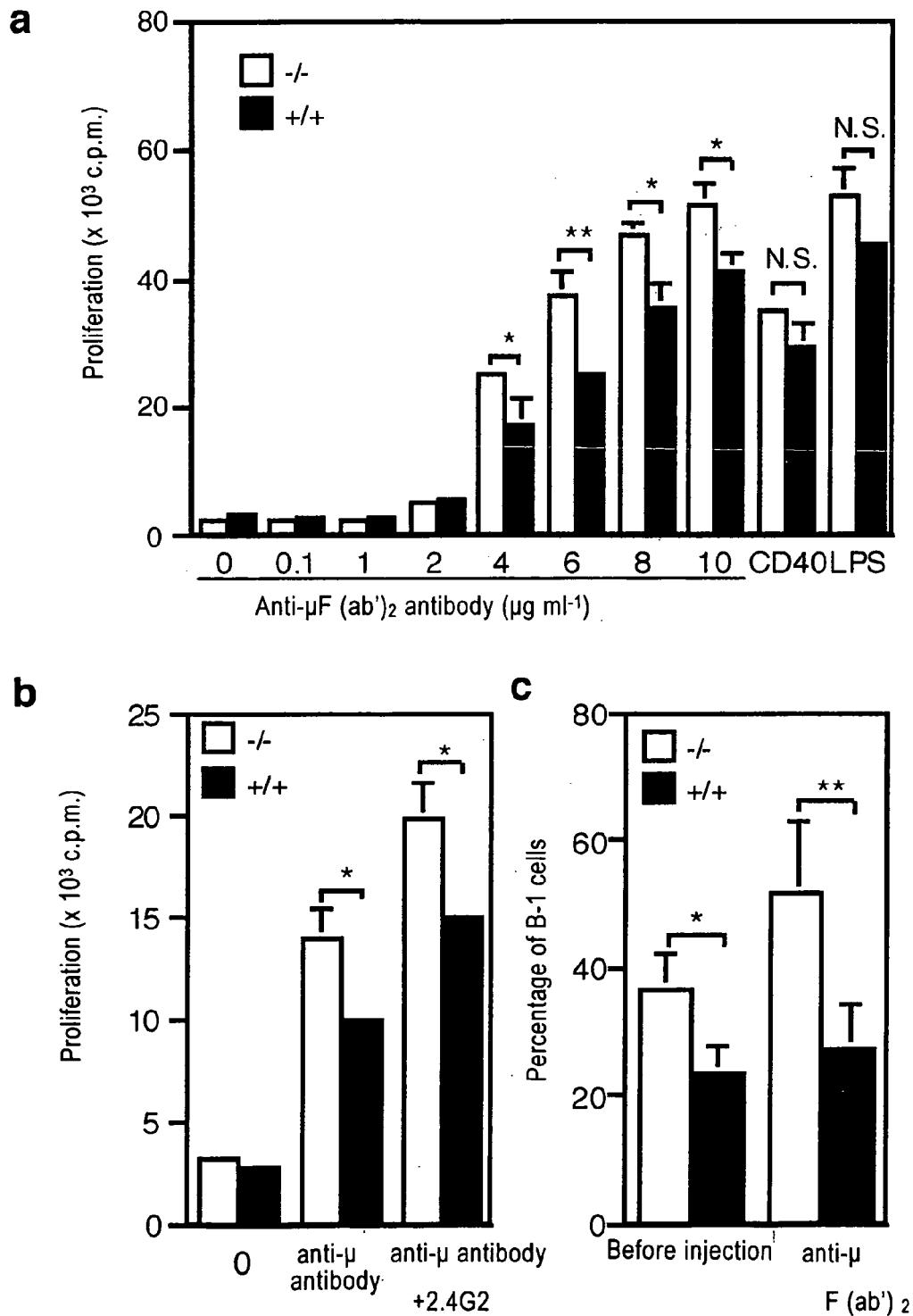

FIG. 3 shows graphs indicating the results of proliferative responses of B cells derived from PIR-B-deficient mice of the present invention to BCR stimulation.

(a) B220 positive splenic B cells obtained from wild-type mice (closed column) and those from PIR-B$^{-/-}$ mice (open column) were cultured in the coexistence of anti-μ F (ab')$_2$ antibody at each of the concentration indicated in the graph, 1 μg/ml of anti-CD40 antibody, or 10 μg/ml of LPS (positive control). The respective results from triplicate experiments are shown as mean values±s.d.

(b) B220 posotive splenic B cells were stimulated with 10 μg/ml of anti-μ antibody in the presence or absence of 25 μg/ml of 2.4G2 to inhibit Fcγ receptor IIB.

(c) Wild-type mice (closed column) or PIR-B$^{-/-}$ mice (open column) were injected with 200 μg of anti-μ (ab')$_2$ antibody intraperitoneally. Before or after 48 h of the injection, ratio of B-1 cell population in peritoneal lymphocytes was estimated by flow cytometry with CD5 and IgM staining. The respective results from triplicate experiments are shown as mean values±s.d. While B-1 cells from wild-type did not respond, those from PIR-B$^{-/-}$ mice proliferated by the anti-μ antibody stimulation. In the graphs, "*", "**", and N.S. represent p<0.05, p<0.01, and not significant, respectively.

Figure 4:
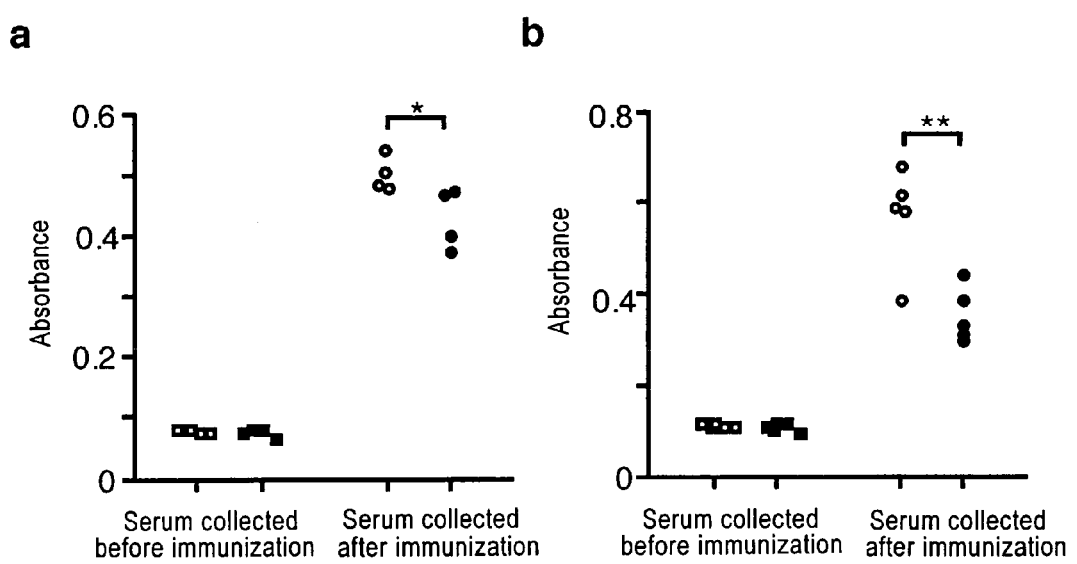

FIG. 4 shows graphs indicating the results of examination of humoral response to T1 antigens in PIR-B$^{-/-}$ mice of the present invention or wild-type mice.

Wild-type and PIR-B$^{-/-}$ mice at 8 weeks of age were immunized with 100 μg of TNP-Ficoli (a) or 50 μg of TNP-LPS (b). Relative amounts of TNP-specific IgM were determined by ELISA. The sera collected before immunization (pre-immune) and the sera collected on the 7th day from immunization (immune) were determined with absorbance at 450 nm. In the graphs, open symbols and closed symbols represent the data of PIR-B$^{-/-}$ mice and of wild-type mice, respectively, and "*" and "**" represent p<0.05 and p<0.01, respectively.

Figure 5:
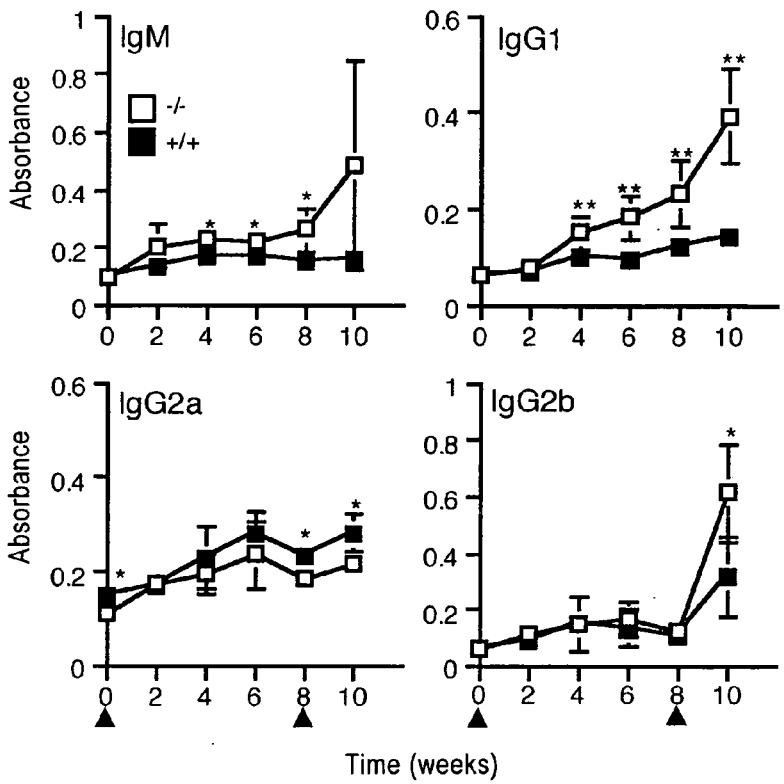
Figure 5:
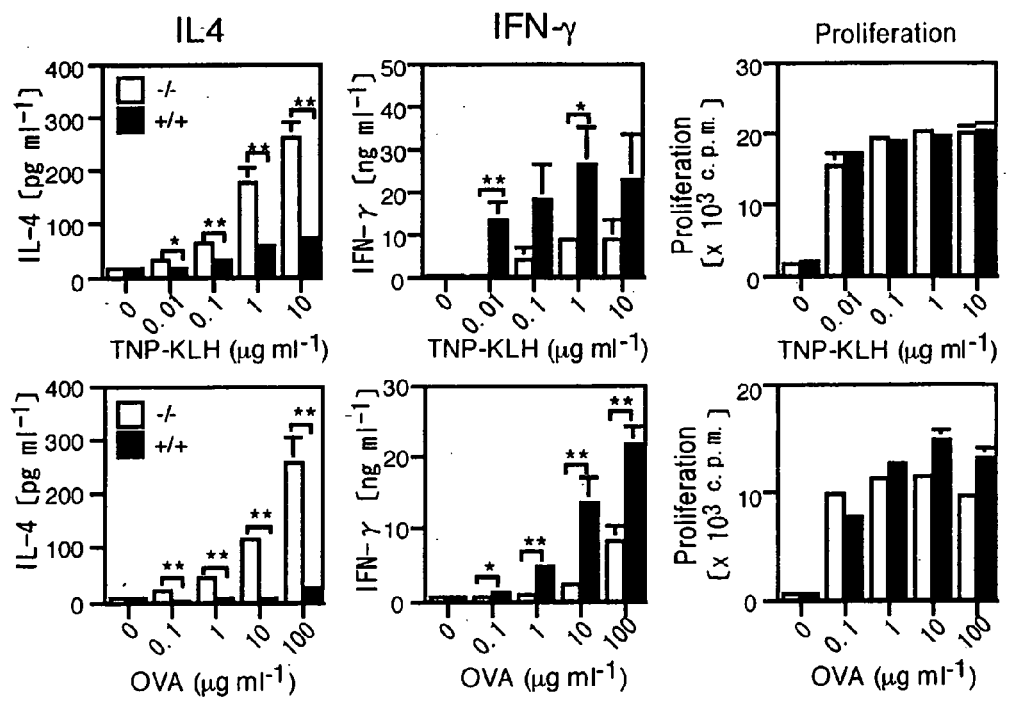

FIG. 5 shows graphs indicating the results of Th2-mediated immune responses to TD antigens in PIR-B$^{-/-}$ mice of the present invention or in wild-type mice.

(a) This shows graphs indicating the result of the examination of humoral response to TNP-KLH. In order to measure immune response to thymus-dependent antigens (TD antigens), wild-type mice (closed squares: n=5) or PIR-B$^{-/-}$ mice (open squares: n=5) at 8 weeks of age were immunized with the mixture of 10 μg of TNP-KLH and 0.25 μg of pertussis toxin with alum adjuvant intraperitoneally. Further, in order to observe the secondary immune response, mice were injected with the mixture of 1 μg of TNP-KLH and 0.25 μg of pertussis toxin with alum adjuvant intraperitoneally at 8th week from the primary immunization. Blood was collected before and at every 2 weeks after the immunization. The titer of anti-TNP antibody in serum was determined by ELISA. In the graphs, arrowheads represent the points at which mice were immunized (at 0 and 8 week). With the use of ELISA, relative amounts of TNP-specific IgM, IgG1, IgG2a and IgGb were determined (absorbance: 450 nm). In the graphs, "*" represents p<0.05.

(b) This shows graphs indicating enhanced IL-4 production and reduced IFN-γ production of lymphocytes from PIR-B$^{-/-}$ mice to antigen. In order to examine the response of T-cells in immune response to TD antigens, mice were immunized onto their foodpads with the mixture of 10 μg of TNP-KLH (upper panel) or OVA (lower panel) and 0.25 μg of pertussis toxin with alum adjuvant. After 11 days from the primary immunization, popliteal lymph nodes were taken out from wild-type mice (closed column) or PIR-B$^{-/-}$ mice (open column) to collect lymph node cells, and the lymph node cells from wild-type or PIR-B-deficient mice were re-stimulated with TNP-KLH or OVA. After 40 h from stimulation, the culture supernatant was collected to determine IL-4 or IFN-γ in it by ELISA. Proliferation of lymph node cells was determined by [$^3$H]-thymidine uptake on the 3rd day from the culture. Mean values (±s.d.) of triplicate cultures are shown as data. Two independent experiments were conducted to obtain theses results, which were similar to each other. In the figure, "*" and "**" represent p<0.05 and p<0.01, respectively.

Figure 6:
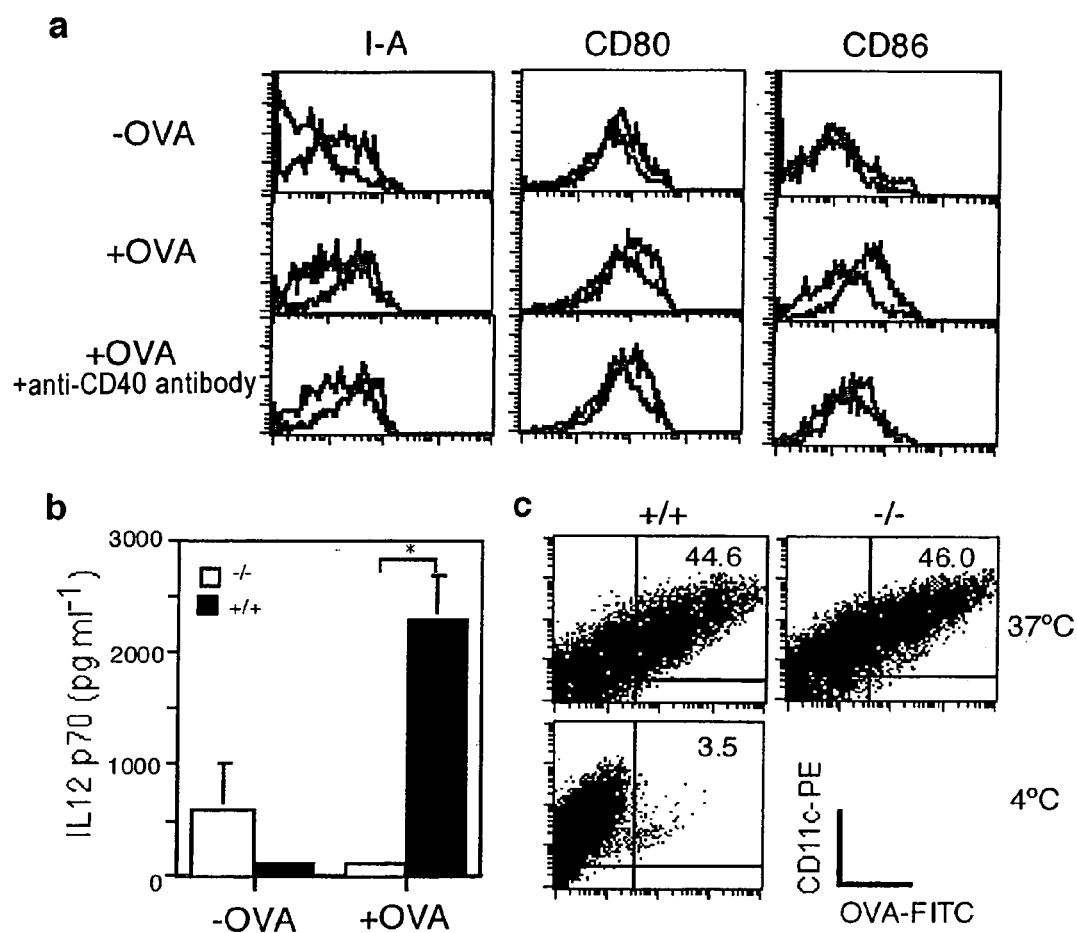

FIG. 6 shows graphs indicating the results of impaired maturation of DCs and reduced IL12 production in PIR-B$^{-/-}$ mice of the present invention.

(a) This shows graphs indicating the results of examining DC maturation. DCs from wild-type mice (bold line) or PIR-B$^{-/-}$ mice (light-colored line) were incubated for 24 h in the presence or absence of OVA or anti-CD40 antibody. The above-mentioned DCs were then stained and analyzed by flow cytometry so as to examine the expression of MHC class II (I-A), CD80, or CD86. In DCs from wild-type mice, increased expressions were shown in all three molecules mentioned above, indicating an efficient DC maturation. Whereas, in DCs from PIR-B-deficient mice, impaired DCs maturation was suggested by decline of 1-A expression level and apparent reduction of CD80 and CD86 expression.

(b) This is a graph showing DCs producing IL12p70 in response to OVA during 24 h-culture. Data is shown as the mean values (±s.d.) of triplicate cultures. In the graph, "*" represents p<0.05.

(c) This shows graphs indicating DCs from wild-type and PIR-B$^{-/-}$ mice uptaking antigen. DSc were incubated in the coexistence of FITC-conjugated OVA at 37° C. or 4° C. for 3 h, washed, and then stained with PE-conjugated anti-CD11c antibody. FITC-labeled OVA uptake by DCs was monitored by flow cytometry. There was no significant difference in amount of antigen uptake between DCs from wild-type and from PIR-B-deficient mice.

BEST MODE FOR CARRYING OUT THE INVENTION

In the present invention, a nonhuman model animal of Th2-mediated hyperimmune response refers a nonhuman animal which shows hyper-response of B cells and characteristic Th2-prone humoral responses and which is liable to suffer from allergy and the like, for example a nonhuman animal whose PIR-B (p91A) gene (J. Biol. Chem. 272, 7320-7, 1997; Proc. Natl. Acad. Sci. USA. 94, 5261-6, 1997; J. Biochem. 123, 358-68, 1998) function is deficient on its chromosome or the like can be specifically exemplified, however, it is not particularly limited to them. The nonhuman animal develops allergy more excessively than a wild-type nonhuman animal by immunizing adjuvant that initiates Th2-mediated response such as alum adjuvant comprising TNP-KLH and pertussis toxin. The aforementioned nonhuman animal lacking PIR-B gene function on its chromosome refers a nonhuman animal whole or part of whose endogenous gene that encodes PIR-B is inactivated by genetic mutation such as distraction, defect and replacement and that lost function to express PIR-B. Additionally, a rodent such as a mouse, a rat, and the like can be specifically exemplified as the nonhuman animal of the present invention, however, it is not particularly limited to them.

The wild-type nonhuman animal of the present invention means an animal of the same species as the above-mentioned nonhuman animal lacking PIR-B gene function on its chromosome, a littermate animal is preferably exemplified above all. It is desirable to use PIR-B-deficient type in these homozygotic nonhuman animals which were born at the expected Mendelian ratios and their littermates of wild-type simultaneously, because precise comparative experiment can be conducted at an individual level. As a preferable example of the nonhuman model animal of Th2-mediated hyperimmune response of the present invention and a wild-type nonhuman animal, PIR-B knockout mice and wild-type of littermates of the PIR-B knockout mice are specifically exemplified, respectively. The case where a nonhuman animal is a mouse is explained with examples below.

A mouse lacking PIR-B gene function on its chromosome, i.e., PIR-B knockout mouse (PIR-B$^{-/-}$) is generated. PIR-B knockout mouse can be generated by the method such as described in the article (Nature 379, 346-349, 1996). In particular, a PIR-B gene is screened with a gene fragment obtained from a mouse genomic library by PCR or other such method, whole or part of the screened PIR-B gene is replaced with a marker gene such as neomycin-resistant gene by technique of DNA recombination, a gene such as a diphtheria toxin A fragment (DT-A) gene or a herpes simplex virus thymidine kinase gene (HSV-tK) is introduced into 5'-terminal side to construct a targeting vector, the constructed targeting vector is linearized and introduced into ES cells by a method of such as electroporation, then the ES cells are homologously recombined, and subsequently the ES cells showing resistance against antibiotic such as G418 or ganciclovir (GANC) among the recombinant are selected. It is preferable to confirm by Southern blotting etc. whether these selected ES cells are object recombinants.

The above-mentioned recombinant ES cell is microinjected into blastocyst of mouse, and the blastocyst is transplanted into a uterus of a recipient mouse to generate a chimeric mouse. A heterozygote mouse can be obtained by intercrossing the chimeric mouse with a wild-type mouse, and PIR-B knockout mouse can be generated by intercrossing the heterozygote mice. In addition, as a method for confirming whether PIR-B gene in the PIR-B knockout mouse is deficient PIR-B cells on its chromosome, a method for examining with Southern blotting and others by isolating DNA from splenic B cells of the mouse obtained from above-mentioned method, and a method for examining with immunoblot analysis and others by using protein extracted from splenic B cells of this mouse, can be exemplified.

The nonhuman model animal of Th2-mediated hyperimmune response of the present invention is useful for analyzing the Th2-mediated immune response mechanism and allergy onset mechanism. Because the nonhuman model animal of Th2-mediated hyperimmune response lacking PIR-B gene function of the present invention induces inhibition of Th2-mediated hyperimmune response and the inhibition of PIR-A function is suggested, the nonhuman model animal of Th2-mediated hyperimmune response of the present invention can be used for screening a substance which controls these biological responses. That is, using the nonhuman model animal of Th2-mediated hyperimmune response allows not only to screen an inducer/inhibitor for Th2-mediated immune response such as a substance comprising the same inhibitory action as PIR-B, an inducer/promoter for Th2-mediated immune response such as a substance promoting Th2-mediated immune response induction, a promoter for PIR-A function such as a substance enhancing PIR-A function which is declined in the nonhuman model animal of Th2-mediated hyperimmune response of the present invention, an inhibitor for PIR-A function such as a substance inhibiting PIR-A function further, a therapeutic agent for an allergosis and the like but also to diagnose of an allergosis.

As a method for screening an inducer/promoter or an inhibitor for Th2-mediated immune response or a promoter or an inhibitor for PIR-A function, a method for measuring/evaluating the alteration of Th2-mediated immune response such as alternation of activation of B cells, generation of antibodies, production of cytokine, antigen presentational ability in the antigen presenting cells, or PIR-A function by administering the test substance to the nonhuman model animal of Th2-mediated hyperimmune response of the present invention or contacting the tissue, the organs or the cells from the nonhuman model animal of Th2-mediated hyperimmune response to the test substance can be specifically exemplified but it is not limited to them. As a method for measuring/evaluating the alteration of activation of B cells, for example, a method for measuring/evaluating activation of B cells such as development of B cells, proliferation of B cells, sensitivity of B cells such as B-1 cells or B-2 cells for binding with BCR in condition with and without the test substance to specify a substance in which alteration has occurred, can be exemplified. As a method for measuring/evaluating the alteration of generation of antibody, for example, a method for measuring/evaluating increase or decrease of generation of antibody such as IgM antibody, IgG1 antibody, IgG2b antibody, IgG2a antibody in condition with and without the test substance to specify a substance in which alteration has occurred, can be exemplified. As a method for measuring/evaluating the alteration of production of cytokine, for example, a method for measuring/evaluating increase or decrease of production of cytokine such as interleukine-4, IFN-γ, interleukine-12 in condition with and without the test substance to specify a substance in which alteration has occurred, can be exemplified. Further, as a method for measuring/evaluating the alteration of antigen presentational ability in antigen presenting cells, for example, a method for measuring/evaluating increase or decrease of expression amount of antigen which is specific to antigen presenting cells such as a major histocompatibility complex class II, CD80, CD86 and the like in antigen presenting cells such as dendritic cells in condition with and without the test substance to specify a substance in which alteration has occurred, can be exemplified. Though above-mentioned methods for measuring/evaluating are not limited to these specifically, in screening an inducer/promoter or an inhibitor for Th2-mediated immune response, or a promoter or an inhibitor for PIR-A function, it is more preferable to compare/evaluate the nonhuman model animal of Th2-mediated hyperimmune response with the wild-type nonhuman animal of its littermate.

As a method for screening a therapeutic agent for an allergosis, for example, a method for measuring/evaluating the alteration of Th2-mediated immune response such as activation of B cells, generation of antibodies, production of cytokine, antigen presentational ability in antigen presenting cells, and the like or PIR-A or PIR-B function by administering the test substance to the nonhuman model animal of Th2-mediated hyperimmune response of the present invention or contacting the tissue, the organs or the cells from the nonhuman model animal of Th2-mediated hyperimmune response to a test substance to specify the substance in which Th2-mediated immune response or PIR-A or PIR-B function is improved, can be exemplified, but it is not limited to these methods. As a method for measuring/evaluating the alteration of activation of B cells, for example, a method for measuring/evaluating activation of B cells such as development of B cells, proliferation of B cells, sensitivity of B cells such as B-1 cells or B-2 cells for binding with BCR in condition with and without the test substance to specify a substance in which the activation of B cells has been improved can be exemplified. As a method for measuring/evaluating the alteration of generation of antibody, for example, a method for measuring/evaluating increase or decrease of generation of antibody such as IgM antibody, IgG1 antibody, IgG2b antibody, IgG2a antibody in condition with and without the test substance to specify a substance in which generation of antibody has been improved can be exemplified. As a method for measuring/evaluating the alteration of production of cytokine, for example, a method for measuring/evaluating increase or decrease of production of cytokine such as interleukine-4, IFN-γ, interleukine-12 in condition with and without the test substance to specify a substance in which production of cytokine has been improved, can be exemplified. Further, as a method for measuring/evaluating the alteration of antigen presentational ability in the antigen presenting cells, for example, a method for measuring/evaluating increase or decrease of expression amount of antigen specific to antigen presenting cells such as the major histocompatibility complex class II, CD80, CD86 in the antigen presenting cells such as dendritic cells in condition with and without the test substance to specify a substance in which antigen presentational ability in the antigen presenting cells has improved, can be exemplified. Though above-mentioned methods for measuring/evaluating are not limited to these specifically, it is more preferable to compare/evaluate the nonhuman model animal of Th2-mediated hyperimmune response with the wild-type nonhuman animal of its littermate in screening a therapeutic agent for an allergosis in respect of confirming whether there is a side-effect.

As candidate substances for an inducer/promoter or an inhibitor for Th2-mediated immune response or a promoter or an inhibitor for PIR-A function obtained from the method for screening an inducer/promoter or an inhibitor for Th2-mediated immune response or a promoter or an inhibitor for PIR-A function of the present invention, substances such as prostaglandin E2 (PGE2), phospholipase A2 (PLA) can be exemplified. Further, as therapeutic agents for allergosis such as anaphylactic shock, bronchial asthma, and pollen allergen obtained from the method for screening a therapeutic agent for an allergosis of the present invention, therapeutic agents comprising the aforementioned inducer/promoter or the inhibitor for Th2-mediated immune response or the inducer/promoter or the inhibitor for PIR-A function as effective ingredients are exemplified, but they can be not limited to these.

The inducer/promoter or the inhibitor for Th2-mediated immune response or the promoter or the inhibitor for PIR-A -function of the present invention obtained from the above-mentioned method for screening can be used for therapy for such as a patient requiring induction/promotion or inhibition of Th2-mediated immune response or promotion or inhibition of PIR-A function, or a patient developing a disease by Th2-mediated hyperimmune response such as allergosis. A therapeutic agent for an allergosis of the present invention can be administered orally or parenterally. For oral administration agent, it refers pharmaceutical solid such as powder, granule, capsule, and tablet or liquid pharmaceutical such as syrup and elixir, while for parenteral administration agent, it refers injection, percutaneous pharmaceutical or suppository. These formulations can be manufactured by adding auxiliaries accepted pharmacologically and pharmaceutically to active ingredients in a conventional manner. As auxiliaries, in oral agent and mucosal administration agent, ingredients for formulation, e.g. diluents such as light silicic acid anhydride, starch, lactose, crystalline cellulose, lactose calcium, disintegrant such as carboxymethyl cellulose, lubricant such as magnesium stearate and others, in injectable solution, ingredients for formulation e.g. solubilizer and auxiliary solubilizer agent such as saline, mannitol and propylene glycolate, suspending agent such as surfactant and others, and further, in external preparation, ingredients for formulation, e.g. aqueous or oleaginous solubilizer or auxiliary solubilizer agent and adhesive are used. In addition, applied dose is suitably determined according to the kind of subjected disease, age, sex, weight, symptoms of a patient, and a dosage form.

The present invention will be explained more specifically with examples below, but the technical scope of the invention is not limited to these examples.

EXAMPLE 1

Generation of PIR-B-Deficient Mice

Phage clones containing the 8.8 kb of mouse PIR-B gene were isolated from the genomic library of 129/SvJ (Stratagene) with intracellular region of B10A-derived PIR-B cDNA (1.0 kb of Eco RI-Xho I fragment) as a probe. 5.0 kb of Eco RV-Eco RI fragment containing the region of exons 1-7 and 5' side of exon 8 was cut out and recloned into pBlueSK+cleaved with Hin cII-Eco RI. This was cleaved with Xba I, filled up, and added with Sal I linker to make 5.0 kb of Xho I-Sal I fragment to be 5'-side fragment. Another subclone containing exons 10-14 was used as a template, 2.0 kb of fragment was amplified by PCR using the primer added with Xho I linker on 5'-side (primer 1: 5'-TATCCTC-GAGCTTCTCCGACGAAGACATCG-3'; Seq. ID No. 1) and the primer added with Sal I linker on 3'-side (primer 2: 5'-AGATCGTCGACTGTTCAGTTGTTCCCTTGAC-3'; Seq. ID No. 2) to make 2.0 kb of Xho I-Sal fragment of post-cleavage of Xho I-Sal I was made to be 3'-side fragment. 5.0 kb of 5'-side fragment and 2.0 kb of 3'-side fragment were integrated into Xho I site and Sal I site of pMC1-Neo vector which does not comprise Poly-A additional signal (pMC1-Neo-pA$^-$; Stratagene), respectively. It was then cleaved with Xho I-Sal I, and 8.0 kb fragment was integrated into the Xho I site of pIC19R-MC1tK vector containing a herpes virus thymidine kinase to construct PIR-B targeting vector (FIG. 1a; exons 9 and 10 are transmembrane regions). The vector was cleaved with Cla I site in the polylinker of the plasmid and linearized.

The ES cell lines RW4 ($10^7$ cells) maintained on feeder layer from primary embryonic fibroblasts (37° C., 5% $CO_2$) and 25 μg of PIR-B targeting vector were suspended into 600 μl of phosphate buffered saline (PBS-), and electroporated at 800 V with 3 μF of capacitance using 4 cm wide cuvettes. After 10 min, the cells were infused separately into 60 mm dishes by $10^6$ cells. After 48 h, selection was begun with 400 μg/ml of G418 and 0.2 μM of FIAU, the concentration was lowered to 300 μg/ml of G418 from the 5th day and to 225 μg/ml of G418 on the 7th day, G418 was completely removed on the 8th day, and grown colonies (184 colonies) were picked up onto 96-well plates on the 10th day. Three days thereafter, they were subcultured onto 24-well plates, further three days thereafter, half of them were cryopreserved and the rest of them were enlarged for DNA recovery, and two days later DNA was recovered. Homologous ES cell recombinants were obtained at a frequency of 2.2% (4 cells) by Southern blotting analysis. The homologous ES cell recombinants were injected into blastocysts to generate chimeric mice. The chimeric mice were confirmed by Southern blotting analysis with the use of probes showing genomic DNA extracted from mouse splenic B cells in FIG. 1 (FIG. 1b). As a result, it was found that 4 male chimeric mice had germline transferability. The above-mentioned male chimeric mice were intercrossed with C57BL/6J female mice, heterozygous mice were generated from the littermates, and the heterozygous mice were then intercrossed to generate homozygous mice at the expected Mendelian ratios. Further, although the homozygous mice showed normal growth, when PIR-B expression in splenic B cells of PIR-B-deficient mice was analyzed in protein level by immunoblotting, disappearance of PIR-B expression was confirmed (FIG. 1c). Then, following examples were conducted with aforementioned PIR-B gene-deficient and wild-type mice at 6-32 weeks old.

It has been apparent that PIR-A and PIR-B co-express in a wide variety of cells in the immune system such as B cells, mast cells (MCs), dendritic cells (DCs) and macrophages at least in mRNA level or reverse transcriptase-polymerase chain reaction (RT-PCR) level (Proc. Natl. Acad. Sci. USA. 94, 5261-5266, 1997; J. Exp. Med. 189, 309-318, 1999; J. Biochem. 123, 356-368, 1998). Flow cytometric analysis (J. Exp. Med. 189, 309-318, 1999) of bone marrow-derived macrophages (BM-Macrophages) or bone marrow-derived dendritic cells (BM-DCs) using a monoclonal antibody 6C1 that recognizes a common epitope of PIR-A and PIR-B showed the reduction of PIR expression in cells from PIR-B$^{-/-}$ mice, suggesting that these cell types co-express PIR-A and PIR-B on their surfaces. That is, it is shown that PIR-A dominates PIR-B in BM-macrophages, whereas PIR-B dominates PIR-A in BM-DCs (FIG. 1d). On the other hand, analysis of BM-MCs and splenic B cells revealed that PIR-B expresses exclusively on these cell surfaces because the PIR staining was almost gone in the cells from PIR-B$^{-/-}$ mice (FIG. 1d). The aforementioned results in normal cells and cells from PIR-B$^{-/-}$ mice elucidated respective expression profiles of PIR-A and PIR-B on each cell in immune system, and these results and description in articles (Proc. Natl. Acad. Sci. USA. 94, 5261-5266, 1997; J. Biochem. 123, 358-368, 1998) suggested the importance of PIR-A/B expression balance on each immune systemic cell for immune regulation. On the other hand, expression balances of murine IgLR, gp49A and gp49B are known to be specific according to cell-types (Mol. Cell. Biol. 20, 7178-7182, 2000).

EXAMPLE 2

Flow Cytometric Analysis of B Cell Development in Wild-Type and PIR-B$^{-/-}$ Mice Splenic CD4/CD8 T cells and T/B cell population ratios were not significantly changed in PIR-B$^{-/-}$ mice, suggesting that PIR-B deficiency does not influence general T cell development. On the other hand, Kubagawa et al. has reported that the expression of PIR molecules is regulated in each process of B cell development, maturation and activation (J. Exp. Med. 189, 309-318, 1999). It is reported that PIR expression levels are highest on marginal zone B cells, and they are higher in the peritoneal B-1 B cells than those in B-2 B cells (J. Exp. Med. 189, 309-318, 1999). Then, examination of the expression of molecule in each cell from PIR-B$^{-/-}$ mice showed a normal profile in expression of B220 and IgM in bone marrow cells from PIR-B$^{-/-}$ mice (FIG. 2a). When splenic B cells from PIR-B$^{-/-}$ mice were compared with those from wild-type, it was confirmed that splenic B cells from PIR-B$^{-/-}$ mice contained IgM$^{lo}$ and IgD$^{hi}$ of mature recirculating follicular B cells and IgM$^{hi}$ IgD$^{hi}$ of type 2 transitional B cells (T-2 B cells) equivalent to those from wild-type, but slightly increasing in type 1 transitional B cells (T-1 B cells) of immature type IgM$^{hi}$ IgD$^{lo}$ (FIG. 2b). CD23$^-$CD21$^+$ marginal zone B cells, CD23$^+$CD21$^+$ follicular B cells and CD23$^-$CD21$^-$ B cells in B220$^+$ splenic cells could be observed in PIR-B$^{-/-}$ mice at levels comparable to those of wild-type mice (FIG. 2c).

Meanwhile, CD5$^+$IgM$^+$ peritoneal B-1 cells were more significantly increased in PIR-B$^{-/-}$ mice compared with those of wild-type mice, [FIG. 2d; Mean values % ±SD of B-1 cells were 23.0±4.8 (n=3) in wild-type mice, 36.4±5.6 (n=4) in PIR-B$^{-/-}$ mice, p<0.05, see also FIG. 3b], indicating that the development or increase of the B-1 cell population is promoted by PIR-B deficiency. It is reported that the B-1 cells produce natural antibodies and play an important role in autoimmunity (Annu. Rev. Immunol. 19, 595-621, 2001; Nature 357, 77-80, 1992). Increased B-1 cells are also observed in mice which are deficient in either CD22 (Science 274, 798-801, 1996; Nature 384, 634-637, 1996) or CD72 (Immunity 11, 495-506, 1999), both of which have ITIM(s). However, significant increase of IgM amount in serum could not be detected in PIR-B$^{-/-}$ mice at 6 or 32 weeks of age. In addition, anti-double stranded DNA antibodies could not be detected at least up to 32 weeks of age in PIR-B$^{-/-}$ mice in contrast to CD22-deficient mice, in which hyper IgM and autoantibody production are evident at the same development stage (Science 274, 798-801, 1996; Nature 384, 634-637, 1996).

EXAMPLE 3

B Cell Proliferation Response of PIR-B-Deficient Mice to BCR

Ho et al. has reported that irrespective of the cell activation status, PIR-B molecules in microphages and B cells were constitutively phosphorylated, and PIR-B in splenocytes were constitutively associated with the SHP-1 and Lyn (Proc. Natl. Acad. Sci. USA. 96, 15086-15090, 1999). In Lyn-deficient mice, PIR-B tyrosine phosphorylation was greatly reduced (Proc. Natl. Acad. Sci. USA. 96, 15086-

15090, 1999) and PIR-B ligation on chicken DT40 cells inhibited the BCR-induced tyrosine phosphorylation of Igα/Igβ, Syk, Btk and PLC-γ2 (Oncogene 18, 2291-2297, 1999) were reported. Further, it was revealed that the deletion of PIR-B induces hypersensitive B cells upon BCR ligation from the constitutive association of SHP-1 with PIR-B, as seen in CD22-deficient mice (Science 274, 798-801, 1996; Nature 384, 634-637, 1996). Here, the present inventors analyzed the proliferative response of splenic B-2 cells upon IgM F (ab)$_2$ antibody stimulation and found a significantly enhanced proliferation of the B-2 cells from PIR-B$^{-/-}$ mice (FIG. 3a). The enhanced proliferation was more significant by masking an inhibitory effect by FcγRIIB which is an unique inhibitory Fcγ receptor on B cells, when stimulated with rabbit IgG anti-IgM antibody (Immunity 3, 635-646, 1995; Nature 379, 346-349, 1996) (FIG. 3b). Injecting wild-type or PIR-B$^{-/-}$ mice with anti-IgM F (ab')$_2$ antibody intraperitoneally and analyzing with flow cytometry, the peritoneal B-1 cells from PIR-B$^{-/-}$ mice showed remarkable proliferation, whereas those from wild-type mice did not show proliferation excessively (FIG. 3c). Since an inhibitory regulator of the response raised by BCR crosslinking in B-1 cells was reported (Science 274, 1906-1909, 1996), in order to examine whether the cell proliferative response raised on co-crosslinkage of BCR increases in PIR-B$^{-/-}$ mice, the cells were stimulated with soluble F (ab')$_2$ IgM antibody, anti-CD40 antibody (CD40), or LPS and examined the proliferation of splenic B220 positive cells from uptake amount of [$^3$H]-thymidine. It revealed that PIR-B$^{-/-}$ cells become hypersensitive status to proliferate by stimulation via ligation with BCR. However, as a result of ligation of splenic B-2 cells from wild-type mice with BCR in vitro, a significant increase of PIR-B expression into the detergent-insoluble membrane fraction could not be observed. It has showed that there is no constitutive association of PIR-B with BCR. Therefore, it is probable that the PIR-B may not be a specific inhibitory co-receptor for BCR. Rather, PIR-B may down-regulate BCR signaling by interacting with any ligand, and B cells might obtain hypersensitivity to stimulation via BCR by PIR-B deficiency generally.

EXAMPLE 4

Immune Response and Proliferation of Lymph Node Cells in PIR-B-Deficient Mice

Then, PIR-B$^{-/-}$ mice were injected with TNP-Ficoll or TNP-LPS as TI antigens to observe the immune responses to various substances from above-mentioned results. The result revealed that anti-TNP IgM antibody responses to respective substances showed significant increases in PIR-B$^{-/-}$ mice compared to those in wild-type mice (FIG. 4a, 4b), being consistent with the results of hypersensitive B cells in PIR-B$^{-/-}$ mice (see Example 3). In order to examine whether PIR-B deficiency influences acquired immune response in vivo, wild-type mice or PIR-B-deficient mice were immunized with TD antigen (TNP-KLH+CFA adjuvant or TNP-KLH+pertussis toxin+alum adjuvant) and antibody titer in serum was measured. The results are shown in FIG. 5a. In immunization with TNP-KLH+pertussis toxin+alum adjuvant initiating Th2-mediated response, compared PIR-B-deficient mice with wild-type mice, it was confirmed that the former showed more increased anti-TNP IgG1 antibody titer or anti-TNP IgM antibody titer at primary immunization response and increased anti-TNP IgG1 antibody or anti-TNP IgG2b antibody and decreases anti-TNP IgG2a antibody titer at secondary immunization than the latter (FIG. 5a). As mentioned above, the increase of IgG1 antibody titer induced by Th2-mediated cytokine and decrease of IgG2a antibody titer induced by Th1 type cytokine in PIR-B-deficient mice suggested that PIR-B might affect the differentiation of T cells into Th1/Th2 in immune response to TD antigens in vivo. There, in order to examine the effect of PIR-B deficiency on activation, differentiation and proliferation of T cells in vivo, wild-type or PIR-B-deficient mice were immunized with TNP-KLH or OVA (ovalbumin) onto their footpads, and production and proliferation of cytokine were measured when lymph node cells from PIR-B$^{-/-}$ mice isolated 11 days later from the immunization were re-stimulated with antigen. The results are shown in FIG. 5b. It showed that IL4 (interleukin 4) production was promoted while IFN-γ production was inhibited, but significant difference could not be found in cell proliferation in PIR-B deficient mice. This suggested that although the difference of activation and proliferative ability of T cells could not be found in wild-type and PIR-B-deficient mice, T cells from PIR-B-deficient mice are prone to Th2-type. This result was not inconsistent with the result that IgG1 increased and IgG2a decreased in PIR-B as seen in generation of antigen.

EXAMPLE 5

Lack of Maturation of PIR-B$^{-/-}$ Mice and Decrease of IL-12 Production

In order to explore how the mechanism for the Th2-exaggerated responses in PIR-B$^{-/-}$ mice was, bone marrow dendritic cells (BM-DCs) were isolated from wild-type or PIR-B$^{-/-}$ mice, the cells were pulsed with OVA, and DCs surface markers were analyzed by flow cytometry before and after the pulse with OVA. The results are shown in FIG. 6a. This revealed that DCs from PIR-B$^{-/-}$ mice were relatively immature. Expression ability of MHC class II before the antigen pulse was lower in DCs from PIR-B$^{-/-}$ mice than those from wild-type mice (FIG. 6a), while CD80 and CD86 expression were comparative in the DCs from PIR-B$^{-/-}$ mice and from wild-type. DCs from wild-type mice after pulse with OVA were confirmed to be well matured and concomitantly the expression of both MHC class II and CD80/86 were enhanced while the enhanced expression of these molecules on DCs from PIR-B$^{-/-}$ mice was minimal. In addition, further stimulation with anti-CD40 antibody failed to improve the relatively immature status of DCs from PIR-B$^{-/-}$ mice. It has been reported that the above-mentioned immature DCs are prone to inducing Th2-dediated response (J. Immunol. 167, 1982-1988, 2001). Then, examination of the production of cytokine IL-12 (Immunity 4, 471-481, 1996) which strongly induced Th1 revealed that generation of IL-12 induced with OVA stimulation greatly diminished DCs from PIR-B$^{-/-}$ mice (FIG. 6b). Moreover, the amount of FITC-labeled OVA incorporated into the DCs could be observed to be comparable between the cells from wild-type and those from PIR-B$^{-/-}$ mice (FIG. 6c). From above results, it seems that the degree of the activation-dependant maturation of DCs upon antigen uptake is irrelevant with PIR-B deficiency. Therefore, it can be thought that PIR-B deficiency restricts DCs in its relatively immature status even when sufficient amount of antigen stimulation is added to the cells.

IgLRs, an immunoreceptor family of cell surface molecules that may play regulatory roles in cellular signaling and in immune responses (Science 290, 84-89, 2000; Activating and Inhibitory Immunoglobulin-like Receptors, 7-15, 2001; Annu. Rev. Immunol. 17, 875-904, 1999) is known to include such as human killer cell IgLR, Ig-like transcript/ leukocyte IgLR/myeloid IgLR (ILT/LIR/MIR), leukocyte-associated IgLR (LAIR), signal induction receptor proteins or SIRP both in mouse and human, murine gp49 molecules and PIR. Each molecule of human ILT/LIR/MIR is considered to be closest relatives of murine PIR (J. Biochem. 123, 358-368, 1998; Activating and Inhibitory Immunoglobulin-like Receptors, 7-15, 2001; Proc. Natl. Acad. Sci. USA. 21, 13245-13250, 2000). The present invention revealed that PIR-B has physiological role to negatively regulate the peritoneal B-1 cells, B cell sensitivity to BCR stimulation, humoral response to TI antigen, Th2 response to TD antigen and the like. Although it is suggested that MHC class I molecule may interact with PIR based on the report that PIR phosphorylation was decreased in B2-microgloblin-deficient mice (Proc. Natl. Acad. Sci. USA. 96, 15086-15090, 1999), attempts to identify the PIR-specific ligand have not been successful yet. The present invention can not only analyze how the activation threshold for B cells is determined by PIR-B but also elucidate the ligand for PIR-B based on the result from consideration of B cells and DCs. Specifically, ligand can be identified by preparing fusion protein of PIR and examining interaction with the targeted cells. Further, in PIR, the molecular mass of protein from targeted cells is identified by Western blotting analysis, the candidate protein is prepared when the protein is a known molecule and the ligand can be identified by determining the ligation with PIR, because there is high possibility for expression of ligand on T cells.

Experimental Method

Method 1 (Immunobot Analysis)

B220 positive splenic B cells were selected from splenic B cells ($10^8$) by MACS sorting using B220-beads (Miltenyi Biotec) and lysed. Proteins contained in the supernatants of the cell-lysates were separated by SDS-PAGE using a 7.5% gel and transferred onto a PVDF (ImmobilonP, Millipore) membrane. The membrane was incubated under coexistence of goat anti-PIR-A/B antibody (Santa Cruz Biotech), followed by labeling with biotin-linked monkey anti-goat Ig antibody and peroxidase-conjugated streptavidin (Amersham Pharmacia) as the secondary antibodies and visualization.

Method 2 (Antibodies and Flow Cytometry)

Flow cytometric analysis was performed with the use of monoclonal antibodies (all the antibodies used were products of BD PharMingen) such as FITC-, PE-, or biotin-conjugated anti-mouse IgM antibody (R6-60.2), anti-mouse IgD antibody (11-26), anti-mouse CD5 antibody (Ly-1), anti-mouse B220 antibody (RA3-6B2), anti-mouse CD21 antibody (7G6), anti-mouse CD23 antibody (B3B4), anti-c-kit antibody (2B8), anti-CD11b antibody (M1/70), anti-CD11c antibody (HL3), anti-CD80 antibody (16-10A1), anti-CD86 antibody (GLI), CD40 (3/23), anti-MHC class II antibody (M5/114.15.2) and the like. TRI color-conjugated streptavidin (Caltag) was used for staining biotin-antibody. 6C1 of anti-PIR monoclonal antibodies (J. Exp. Med. 189, 309-318, 1999) were provided by Drs. M. D. Cooper and H. Kubagawa (University of Alabama). IgM F (ab')$_2$ antibodies were purchased from ICN Laboratories. Cell surface staining was carried out according to the method publicly known and flow cytometric analysis was performed with a FACS-Calibur using CellQuest software (Becton Dickinson). Dead cells were eliminated from the analysis, and measurement was performed on the basis with propidium iodide staining.

Method 3 (Proliferation Response of B Cells)

Splenic B220 positive cells were purified by MACS (Mylteni). The cells were activated with soluble anti-IgM F (ab')$_2$ antibody, anti-CD40 antibody (CD40) or LPS, and 48 h after the stimulation, proliferation of splenic B220 positive cells was determined by [$^3$H]-thymidine uptake. For proliferation of peritoneal B-1 cells, wild-type or PIR-B$^{-/-}$ mice were intraperitoneally injected with 200 μg of soluble anti-IgM F (ab')$_2$ antibody, respectively and determined in the same manner as the above-mentioned. After 48 h, peritoneal cells from the individual mouse were stained with biotinylated anti-mouse CD5 monoclonal antibody added with phycoerythrin-conjugated streptavidin or FITC-conjugated anti-mouse IgM monoclonal antibody, and the ratio of B-1 (CD5 positive IgM positive) cell populations was analyzed.

Method 4 (Humoral Response and T Cell Proliferation)

Wild-type or PIR-B-gene-deficient mice were intraperitoneally injected with 100 μg of TNP-Ficoll, 50 μg of TNP-LPS, or with OVA lysed in 10 μg of TNP-KLH or aluminium hydroxide to be immunized. The mice were re-stimulated with antigen after 8 weeks of injection of TD antigen to induce the secondary response, and the antibody titer to TNP in serum was determined by ELISA with absorbance at 450 nm. Lymph node cells were collected from popliteal lymph nodes of wild-type and PIR-B$^{-/-}$ mice 11 days after from the primary immunization with TNP-KLH or OVA. The collected cells were activated with either the same antigen as above-mentioned one or T cell mitogen, 40 h after the stimulation, the supernatant was harvested and the yield of IL-4 or IFN-γ in the culture supernatant was determined by ELISA. T cell proliferation was determined by [$^3$H]-thymidine uptake on the 3rd day of the culture.

Method 5 (DC Maturation and Antigen Uptake)

In order to examine BM-DCs, BM cells from wild-type or PIR-B$^{-/-}$ mice were cultured in the presence of recombinant mouse granulocyte-macrophage colony stimulating factor (GM-CSF) (PeproTech), respectively medium was changed on the 4th day, and the cells were further cultured. On the 6th day of the culture, it was observed that the above BS cells expressed MHC class II molecules, CD40, CD80, CD86 and CD11c and became immature DCs. In order to mature the DCs, 50 μg/ml of OVA or 1 μg/ml of anti-CD40 antibody (BD Pharmigen) was added to DC culture 24 h before the harvest of the cells for stimulation. After stimulation, culture supernatants of DC culture were harvested and mouse IL-12 p70 in the supernatants was measured by ElISA (BD Pharmingen). The above cells were then stained with CD80, CD86 and anti-MHC class II antibody as mature cell markers, and analyzed by flow cytometry. So as to measure the amount of antigen uptake by DCs, the DCs were incubated under coexistence of 20 μg/ml of FITC-conjugated OVA (Molecular Probes) at 37° C. or 4° C. for 3 h, then washed and stained with phycoerythrin (PE)-conjugated anti CD11c antibody. Uptake amount of FITC-OVA by DCs at 37° C. was measured by flow cytometry.

INDUSTRIAL APPLICABILITY

A nonhuman model animal of Th2-mediated hyperimmune response of the present invention allows to analyze the Th2-mediated immune response mechanism and allergy onset mechanism in vivo therewith, and it is useful in studying an allergy onset process as well as a hyperimmune response of B cells, and the use of the nonhuman model animal of Th2-mediated hyperimmune response makes it possible to screen therapeutic agents for allergosis such as anaphylactic shock, bronchial asthma, and pollen allergen and to provide the method for treating allergosis.

The invention claimed is:

1. A transgenic mouse model of Th2-mediated hyperimmune response whose genome comprises a homozygous disruption of the PIR-B gene causing a loss of functional PIR-B expression, wherein said homozygous disruption facilitates a hyperimmune response of B cells.

2. The transgenic mouse model of Th2-mediated hyperimmune response according to claim 1, wherein said mouse develops a more severe immune response of B cells than a wild-type mouse by immunizing with an antigen that initiates Th2-mediated response.

3. The transgenic mouse model of Th2-mediated hyperimmune response according to claim 2, wherein the antigen that initiates the Th2-mediated response comprises an alum adjuvant, TNP-KLH and a pertussis toxin.

4. A method for screening an inducer/promoter or an inhibitor for Th2-mediated immune response or a promoter or an inhibitor for PIR-A function, wherein an alteration of Th2-mediated immune response or PIR-A function is determined after administering a test substance to the transgenic mouse model of Th2-mediated hyperimmune response according to claim 1 or contacting a tissue, an organ or cells comprising antigen presenting cells derived from the mouse to the test substance.

5. The method for screening an inducer/promoter or an inhibitor for Th2-mediated immune response or a promoter or an inhibitor for PIR-A function according to claim 4, wherein the alteration of Th2-mediated immune response is an alteration of activation of the B cell, generation of antibody, production of cytokine and/or antigen presentational ability in an antigen presenting cell.

6. The method for screening an inducer/promoter or an inhibitor for Th2-mediated immune response or a promoter or an inhibitor for PIR-A function according to claim 5, wherein the alteration of activation of the B cell is an alteration of development or proliferation of the B cell.

7. The method for screening an inducer/promoter or an inhibitor for Th2-mediated immune response or a promoter or an inhibitor for PIR-A function according to claim 5, wherein the alteration of generation of antibody is an alteration of generation of an IgM antibody, an IgG1 antibody, an IgG2b antibody and/or an IgG2a antibody.

8. The method for screening an inducer/promoter or an inhibitor for Th2-mediated immune response or a promoter or an inhibitor for PIR-A function according to claim 5, wherein the alteration of production of cytokine is an alteration of production of interleukin-4, IFN-γ and/or interleukin-12.

9. The method for screening an inducer/promoter or an inhibitor for Th2-mediated immune response or a promoter or an inhibitor for PIR-A function according to claim 5, wherein the alteration of antigen presentational ability in the antigen presenting cell is an alteration of expression amount of a major histocompatibility complex class II, CD80and/or CD 86 in a dendritic cell.

10. The method for screening an inducer/promoter or an inhibitor for Th2-mediated immune response or a promoter or an inhibitor for PIR-A function according to claim 4, wherein the Th2-mediated hyperimmune response of said transgenic mouse model is further compared/evaluated with that of a wild type mouse.

11. The transgenic mouse model according to claim 1, wherein said transgenic mouse model has an impaired maturation of dendritic cells and a reduction in IL-12 compared to a wild-type mouse.

* * * * *